United States Patent [19]

Ryan

[11] Patent Number: 5,085,639
[45] Date of Patent: Feb. 4, 1992

[54] SAFETY WINGED NEEDLE MEDICAL DEVICES

[75] Inventor: Dana W. Ryan, Franklin, Tenn.

[73] Assignee: Ryan Medical, Inc., Brentwood, Tenn.

[21] Appl. No.: 416,927

[22] Filed: Oct. 4, 1989

Related U.S. Application Data

[63] Continuation-in-part of Ser. No. 162,569, Mar. 1, 1988, and a continuation-in-part of Ser. No. 224,920, Jul. 27, 1988, Pat. No. 4,923,445, and a continuation-in-part of Ser. No. 257,407, Oct. 13, 1988, and a continuation-in-part of Ser. No. 303,588, Jan. 27, 1989.

[51] Int. Cl.$^5$ .............................................. A61M 5/00
[52] U.S. Cl. .................... 604/110; 604/177; 604/198
[58] Field of Search ............... 604/110, 162, 177, 192, 604/194–198, 240–243, 263, 111, 181, 185, 187, 188, 199, 211, 212, 214, 216, 232, 334, 174, 186, 171, 208; 128/760, 762–767, 770, DIG. 26

[56] References Cited

U.S. PATENT DOCUMENTS

| | | | |
|---|---|---|---|
| 4,576,671 | 3/1986 | Shimanaka | 604/177 |
| 4,664,128 | 5/1987 | Lee | 604/187 |
| 4,747,830 | 5/1988 | Gloyer et al. | 604/110 |
| 4,747,837 | 5/1988 | Hauck | 604/198 |
| 4,762,516 | 8/1988 | Luther et al. | 604/192 |
| 4,781,692 | 11/1988 | Jagger et al. | 604/198 |
| 4,790,827 | 12/1988 | Haber et al. | 604/198 |
| 4,846,811 | 7/1989 | Vanderhoof | 604/263 |
| 4,874,384 | 10/1989 | Nunez | 128/919 |
| 4,896,796 | 7/1989 | Carrell et al. | 604/198 |
| 4,923,445 | 5/1990 | Ryan | 604/198 |

FOREIGN PATENT DOCUMENTS

| | | | |
|---|---|---|---|
| 0186232 | 7/1986 | European Pat. Off. | 604/187 |
| 2183484 | 6/1987 | United Kingdom | 604/187 |

Primary Examiner—Randall L. Green
Assistant Examiner—K. M. Reichie
Attorney, Agent, or Firm—David P. Gordon

[57] ABSTRACT

Shielded winged needled medical devices which minimize accidental needlesticks of the skin by an exposed contaminated needle are provided. The medical devices include a hollow inner tube body having a pair of circumferential grooves on the outside thereof, and a slightly larger hollow outer winged shield which is slidable relative to the inner tube. The inner tube has a shoulder of relatively large diameter forwardly adjacent the front groove, and a ramp of diameter smaller than the shoulder rearwardly adjacent the front groove. The outer shield has an inner surface with first and second ramps and a protrusion which terminates the second ramp. The protrusion is arranged such that it sits in the rear groove of the inner tube while the winged needle device is being used. Thereafter, the outer shield may be slid forward relative to the inner tube, overcoming resistance given by the engagement of the protrusion and a ramp forward the rear groove, until the protrusion slides up the ramp rearwardly adjacent the front groove and locks in the forward groove. In this forward position, the now-contaminated needle is shielded. The provided ramps and protrusion on inner surface of the outer shield, and the ramp, groove, and shoulder on the outer surface of the inner shield provide an absolute lock which may not be overcome by manual force.

30 Claims, 3 Drawing Sheets

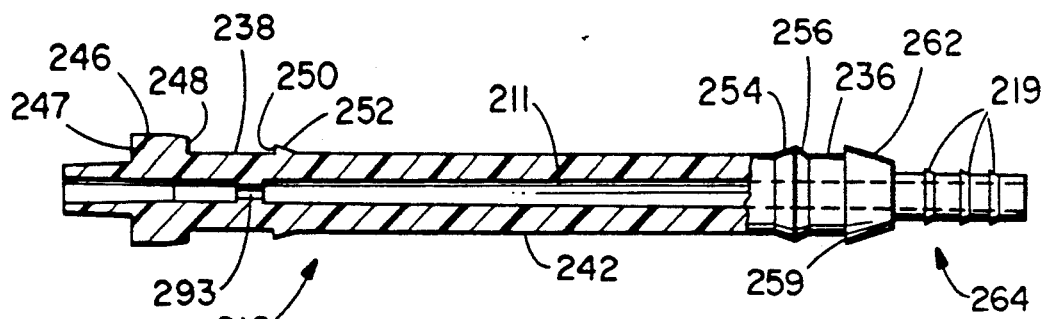
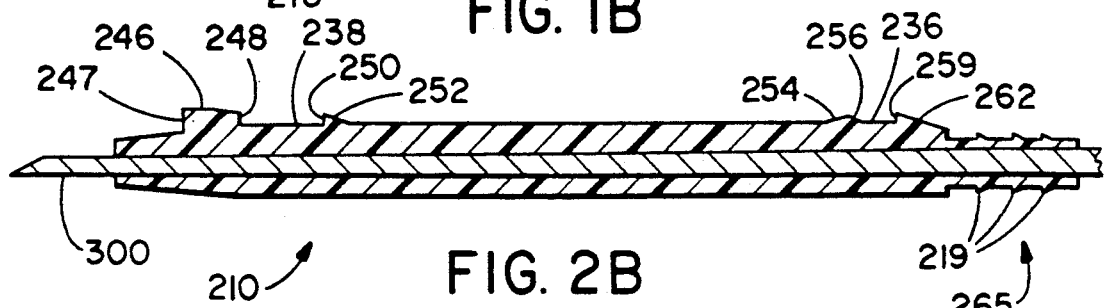
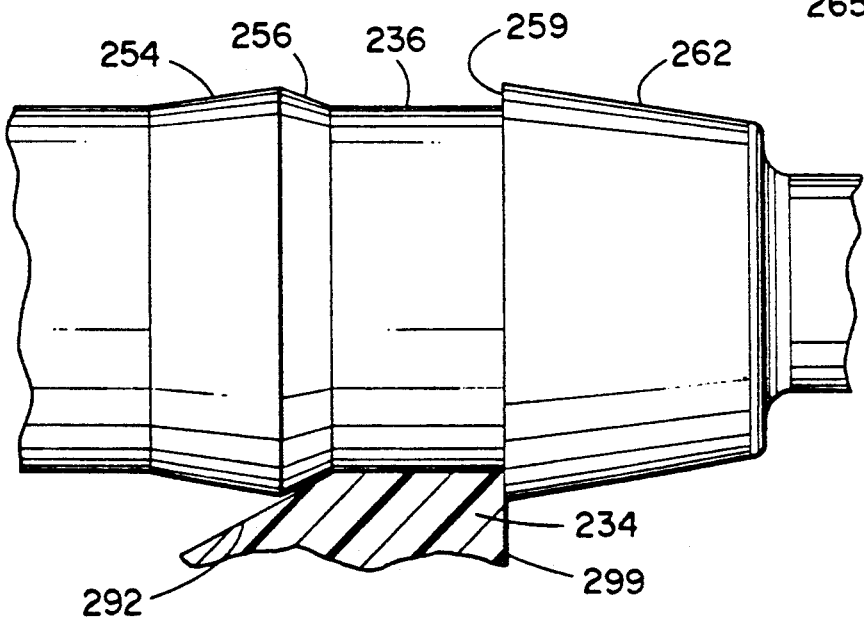
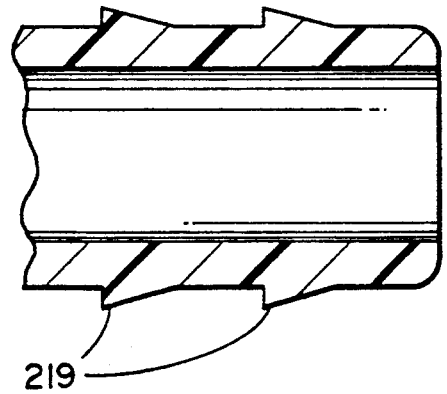

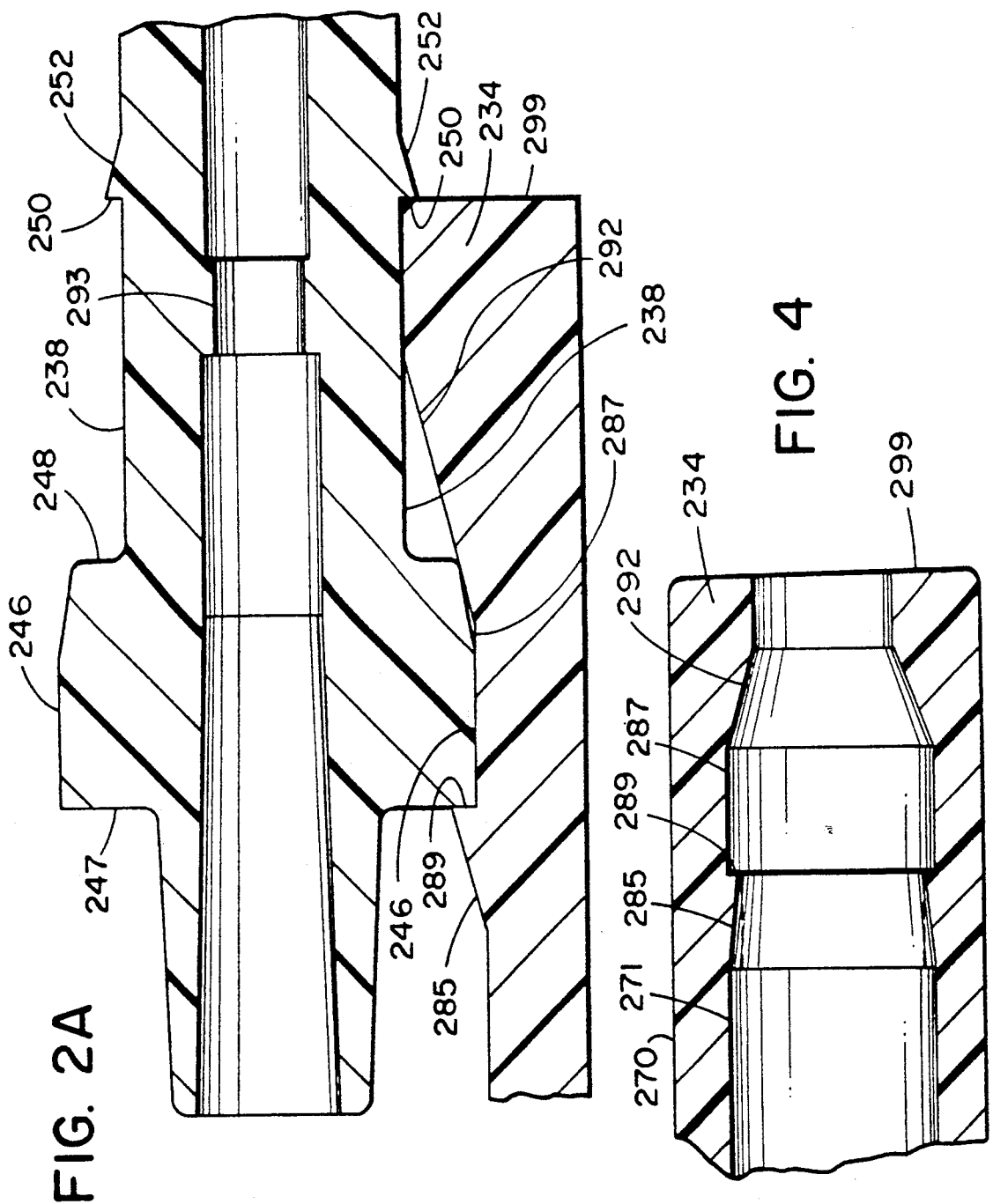

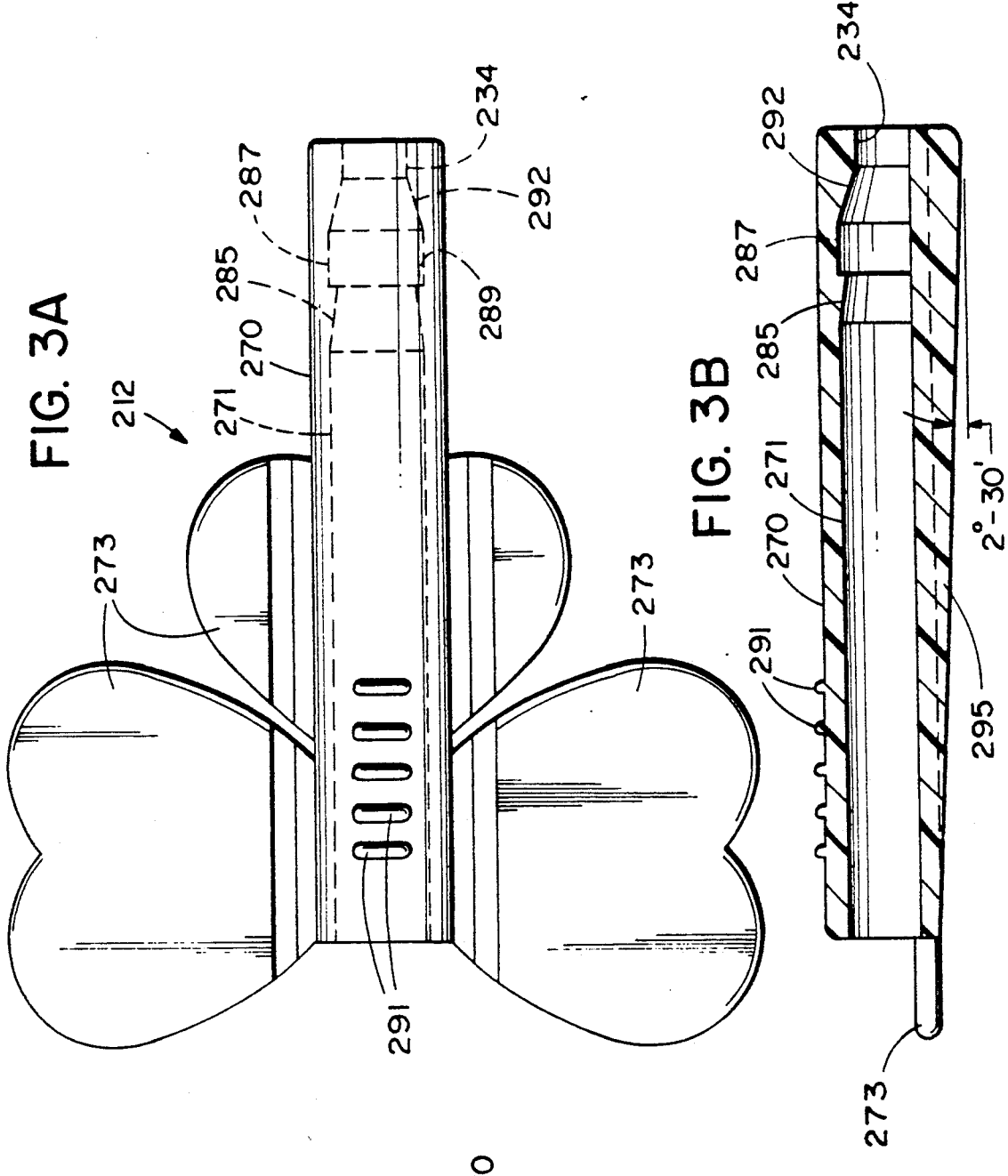

SAFETY WINGED NEEDLE MEDICAL DEVICES

This application is a continuation-in-part of copending Ser. No. 07/162,569, filed Mar. 1, 1988, now allowed Ser. No. 07/224,920, filed July 27, 1988, now U.S. Pat. No. 4,923,445, filed Oct. 13, 1988, now pending and Ser. No. 07/303,588, filed Jan. 27, 1989, now allowed, all of which are hereby incorporated herein.

BACKGROUND OF THE INVENTION

The present invention generally relates to winged needle medical devices. More particularly, the present invention relates to safety winged needle medical devices such as winged blood collection needles, winged infusion needles, winged hemodialysis needles, and blood collection bags with attached winged needles, which are designed to minimize the incidence of accidental needlesticks after needle contamination.

Accidental needlesticks have long been a problem in the medical profession. Accidental needlesticks most often occur during the recapping of a contaminated needle or immediately after use and prior to safe disposal. Such needlesticks place the medical professional (clinician) at risk. When needles are not recapped, additional accidental needlesticks are caused by uncapped needles found in patent beds, linens, and in garbage cans, and place health care, housekeeping and sanitation personnel at risk. Because accidental needlesticks can now result in deadly incurable diseases as well as the previously appreciated serious, but curable diseases, the need for eliminating the needlestick problem has reached extreme urgency. In addressing the urgency, many devices have been proposed. Indeed, reference may be had to the background section of parent application hereof, U.S. application Ser. No. 7/162,569 for a discussion of the prior art of safety needles, as well as the background section of parent application hereof, U.S. application Ser. No. 07/257,407 for a discussion of the prior art relating to winged needle arrangements.

SUMMARY OF THE INVENTION

It is therefore an object of the present invention to provide improved winged needle safety devices which are easy and economical to manufacture and assemble It is a further object of the invention to provide winged needle safety shielded devices which do not require a substantial change of technique and procedure during use and which utilize a locking mechanism in which the movement of a shield from an unshielding position to a locked shielding position may be accomplished in an easy uniform sliding motion.

It is another object of the invention to provide winged needle safety shielded devices having an outer shield and an inner tube, such that in a first position, the outer shield does not shield the intravenous needle attached to the inner tube, and such that in a second position, the outer shield extends over and shields the intravenous needle while locking so completely with the inner tube so as to completely prevent unintended reexposure.

In accord with the objects of the invention, a safety shielded winged needle assembly is provided and is comprised of two cooperating pieces; a hollow inner tube needle adaptor, and an outer hollow shield. If desired, a hollow needle may also be provided as part of the assembly, and the inner tube may be molded around the needle. Where the inner tube is not molded around the needle, the hollow inner tube needle adaptor has a front end adapted to have the hollow needle secured thereto and a back end adapted to have tubing attached thereto. The hollow inner tube has an outer surface having a front shoulder of relatively large diameter. Directly behind the front shoulder is a first groove which is defined on its other side by the termination of a ramped surface which ramps downward away from the groove. The inner tube also includes a second groove which is located towards the rear of the inner tube. The second groove is defined on the rear end by the termination of a ramped surface which ramps downward away from the groove, and on its front end by a ramp which ramps upward away from the groove. The upward ramp is followed by a downward ramp.

The outer shield is formed with an inner surface which cooperates with the outer surface of the inner tube. At the rear end of the outer shield is formed a first, preferably ramped, protrusion which is used to ride over the front shoulder of the inner tube and snap-lock thereover to prevent the outer shield from being retracted thereafter. Following the first protrusion is a groove which is formed to cooperate and sit around the front shoulder of the inner tube. The groove in the inner surface of the outer shield is terminated by a second ramped protrusion. The second ramped protrusion circumscribes a smaller inner diameter than the first protrusion and is arranged so that it cannot be pulled over the front shoulder of the inner tube. The second ramped protrusion is also arranged to sit in but be movable over (i.e. be removably engaged with) the rear groove of the inner sleeve. In this manner, in a first retracted (non-shielding) position the outer shield is engaged with the inner tube such that the shield does not slip off the inner tube; and in a second extended (shielding) position, the outer shield locks with the inner tube thereby covering a contaminated needle and virtually guaranteeing that the contaminated needle will not be reexposed.

Other aspects of the outer shield include wings extending from its outer surface, thumb grip ribs extending from the top of the outer surface, and the shape of the outer shield which is generally semi-circular in cross section. The inner tube shoulder and ramps are also preferably non-cylindrical such that the inner tube cannot rotate relative to the outer shield.

A better understanding of the safety winged needle medical assembly of the invention, and additional objects and advantages of the invention will become apparent to those skilled in the art upon reference to the detailed description and accompanying drawings.

BRIEF DESCRIPTION OF THE DRAWINGS

FIGS. 1a and 1b are top and side plan views, respectively, of the inner tube needle adaptor assembly of the invention, a difference between the inner tube adaptor of FIG. 1a and 1b being that the inner tube of FIG. 1a is adapted for receiving a needle, and the inner tube of FIG. 1b is molded around a needle.

FIGS. 2a, 2b, and 2c are enlarged plan views, respectively, of the front end, the back groove section, and the rear end of the inner tube needle adaptor shown in FIG. 1a, with FIGS. 2a and 2b showing the locking protrusions of the outer shield in engagement;

FIG. 3a is a plan view of the winged shield of the invention;

FIG. 3b is a side plan view of the winged shield of FIG. 3a;

FIG. 3c is a sectional view of a portion of the winged shield of FIG. 3a taken along line c—c of FIG. 3a; and FIG. 4 is an enlarged plan view of the rear end of the winged shield of FIG. 3a.

DETAILED DESCRIPTION OF THE PREFERRED EMBODIMENT

Turning to FIGS. 1a, 1b, and 2a-2c, details of the hollow inner tube needle adaptor 210 are seen. The hollow inner tube has an outer surface 242 having a front shoulder 246 of relatively large diameter. The front shoulder 246 is defined by a front face 247 and a rear abutment face 248. Directly behind the front shoulder 246 is a first groove 238 which is defined on one side by the abutment face 248 and on its other side by the termination (rear abutment face) 250 of a ramped surface 252. The ramped surface 252 starts with a diameter smaller than that of the front shoulder 246 and ramps downward away from the first groove 238. Ramp 252 terminates in a long valley defined by outer surface 242 of needle adaptor 210. The valley has a relatively constant diameter which is preferably substantially equal to the diameter of the first groove 238. The valley ends in a ramp 254 which increases in diameter as it extends away from the front end of the needle adaptor 210. Ramp 254 is followed by ramp 256 which ramps down to a second groove 236. Groove 236 is preferably of a diameter slightly larger than the diameter of the valley, and terminates in a rear abutment surface 259. Surface 259 is also the terminating surface of a rear ramp 262 which ends in the ribbed connecting end 264 of the needle adaptor 210. Connecting end 264 has ribs 219 as indicated for coupling with standard tubing (not shown).

As previously indicated, the inner tube 210 is hollow. In one embodiment, as seen in FIG. 1a, inner tube 210 includes a passage 211 which includes a restriction 293 at the front end. A needle suitable for winged needle applications is inserted in the front end of passage 211 which tapers slightly (as seen in FIG. 2a) as it extends backwards towards a restriction 293 (the opening in the needle having the same diameter as restriction 293). The needle may be suitably cemented in place. As seen in an alternate preferred embodiment of FIG. 1b, no restriction 293 is provided. Rather, inner tube 210 is formed around a needle 300 by insert molding techniques. With such a manufacturing process, the inner tube 210 bonds to needle 300 to prevent relative movement therebetween.

As is best seen in FIG. 1b, the inner tube is preferably non-cylindrical such that inner tube 210 will not rotate inside of outer sleeve 212. With the non-cylindrical shape, shoulder 246, and ramps 252, 254, 256, and 262 do not appear on the bottom of the outer surface of the inner tube 210. Thus, it should be appreciated that when "diameter" dimensions are provided, the term "diameter" is used in a broad sense to indicate relative cross-sectional dimensions. Details of the exact preferred dimensions including both diameters and lengths which permit the inner tube 210 to interact optimally with the outer sleeve 212 are provided below.

Turning to FIGS. 3a-3c, and 4, details of the outer sleeve 212 are shown. Outer sleeve 212 includes flexible wings 273 which are used as means for attachment of the winged needle device to a patient. The flexible wings 273 are attached to the outer surface 270 of the outer sleeve 212. Projecting from the top outer surface 270 of the outer sleeve 212 are thumb grips or ribs 291 which provide the practitioner with a friction surface when utilizing the winged needle device. As indicated in FIG. 3c, the outer sleeve 212 is preferably nearly semicircular in cross-sectional shape, with a flat bottom surface 295. Flat bottom surface 295 is preferably a tapered surface (as seen in FIG. 3b), with the thickness of the bottom increasing according to a two and one half degree slope as it extends away from the front end of the outer sleeve. As a result, when the inner tube and needle are located in the outer sleeve, the needle assumes a downward angle preferably of about two and one half degrees, and is more easily and comfortably inserted into the vein of the patient.

Outer sleeve 212 is hollow and has an inner surface 271 of a diameter slightly larger than the outer diameter of shoulder 246 of the inner tube 210. However, towards its rear end, the inner surface of outer sleeve 212 is arranged with two ramps 285 and 292, although, if desired, ramp 285 may be replaced with a non-ramped protrusion (as indicated in phantom in FIG. 4). As seen in enlarged detail of FIG. 4, ramp 285 provides outer sleeve 212 with a decreasing inner diameter as it extends toward the rear end of the outer sleeve. Ramp 285 terminates in an abutment face 289 which is followed by a flat surface 287 having an inner diameter approximately equal to the outer diameter of shoulder 246 of inner tube 210. Flat surface 287 ends with ramp 292 which has also has a decreasing inner diameter as it extends toward the rear end of the outer sleeve. The inner diameter at the end of ramp 292, however, is of significantly smaller diameter than that of ramp 285. The inner surface of the outer sleeve 212 terminates in a flat protrusion 234 of significantly smaller diameter than the diameter of the shoulder 246.

In assembling the winged needle device, the outer shield 212 and the inner tube 210 are coaxially aligned with the rear portion of the inner tube 210 at the front of the front portion of the outer sleeve 212. Relative movement between the inner tube 210 and outer sleeve 212 causes inner tube 210 to slide through outer sleeve 212 until protrusion 234 engages second groove 236 (as seen in FIG. 2b), with abutment face 259 of inner tube 210 abutting the rear surface 299 of outer shield 212, and with ramp 256 of inner tube 210 engaging ramp 292 of outer sleeve 212. In the assembled position, abutment face 259 serves to keep the inner tube from sliding forward and out of assembly when a tube (not shown) is attached to the rear ribbed portion 264 of the inner tube. At the same time, the location of protrusion 234 in groove 236 serves to prevent the inner tube 210 from sliding backward when the needle (not shown) is inserted into the vein of the patient.

In use, the winged needle assembly including an intravenous needle is held by the practitioner with the wings being squeezed upwards against the outer surface 270 of the outer sleeve 212. The practitioner then uses the needled device to puncture a vein. After venipuncture, the needled device is rested on the arm or body of the patient, and the flexible wings 273 may be used as a taping surface such that the needled device may be taped to the patient. When treatment is completed and it is desired to remove the contaminated needle from the patient, either of two procedures may be utilized. In one procedure, the tape is removed from the arm of the patient and the winged needle device removed. Holding the outer sleeve 212 in one hand such as with thumb on grips 291 and forefinger on bottom surface 295, and gripping the tube (not shown) extending from the ribbed end 264 of the inner tube 210 (and/or from an extended needle) in the other hand, the inner tube 210 is pulled back relative to the outer shield 212 until positive locking is obtained. In a second procedure, before the tape is removed, a finger of the practitioner is placed preferably on the top outer surface of the outer sleeve 212, while the ribbed end 264 of the inner tube 210 (with attached tube—not shown) are gripped with other fingers of the same or a different hand. The inner tube is then pulled back relative to the outer shield until positive locking is obtained, thereby withdrawing the needle from the vein and immediately shielding it in the safety device.

Regardless of the procedure used, in pulling the inner tube back relative to the outer sleeve, some minor initial force is required to overcome resistance of protrusion 234 sliding over ramp 256. However, once the protrusion slides over ramp 256, little force is needed to continue sliding the outer shield over the valley of the inner tube. Extremely minor resistance is encountered when ramp 252 of the inner tube encounters ramp 285 of the outer sleeve. More resistance, however, is encountered when ramp (or protrusion) 285 encounters shoulder 246. With the application of differential force, and due to the ramped nature of ramp 285 and the rounding of the edge of shoulder 246, ramp 285 is slid over shoulder 246 until it snaps over the shoulder 246 with abutment face 289 of the outer shield 212 in contact with abutment surface 247 of the inner tube shoulder. At the same time, protrusion 234 sits in first groove 238 with the rear surface 299 of the outer sleeve abutting abutment surface 250 of the inner tube, and shoulder 246 contacts surface 287. In this locked position, the needle (not shown) is shielded entirely and securely by the outer shield 212. Two locking interactions are established (surface 289 against shoulder 246, and end surface 299 against surface 250) as seen in FIG. 2a to prevent the movement of the inner tube forward and the reexposing of the needle, while the relative sizes of the protrusion 234 and the shoulder 246 prevent any possibility of the outer shield 212 being pulled forward off of the inner tube 210.

In order for the winged needle assembly to function such that locking in the shielded position is irreversible but such that the inner tube can be assembled into an unshielded position which is not inadvertently upset, certain relative diameters and lengths between grooves ramps, etc. of the inner tube and outer shield are desirable. In particular, preferred dimensions are as follows:

| Inner tube portion and # | Length (in) | Outer diameter (in) |
| --- | --- | --- |
| Shoulder 246 | .080 | .150 at 247 .147 at 248 |
| Groove 238 | .114 | .100 |
| Ramp 252 | 15 deg slope | .132 at 250 |
| Valley 242 | .870 | .100 |
| Ramp 254 | 8 deg slope | .133 at peak |
| Ramp 256 | 29.5 deg slope | |
| Groove 236 | .049 | .116 |
| Ramp 262 | .073 | .138 at 259 |

| Outer shield portion and # | Length (in) | Inner diameter (in) |
| --- | --- | --- |
| Inner surface 271 | .980 | .152 |
| Ramp 285 | 8 degree slope | .135 at 289 |
| Inner surface 287 | .080 | .152 |
| Ramp 292 | 20.5 deg slope | |
| Protrusion 234 | .047 | .118 |

With the listed dimensions, and using an inner tube made of polypropylene and an outer shield made of a combination of polypropylene (70% by weight) and kraton (30% by weight), once the shield is locked in the shielding position, it is virtually impossible to force relative movement between the inner tube and outer shield which would reexpose the contaminated needle.

There has been described and illustrated herein safety winged needle devices for use in blood collection, hemodialysis, and intravenous infusion. While particular embodiments of the invention have been described, it is not intended that the invention be limited thereby, as it is intended that the invention be as broad in scope as the art will allow. Thus, while exact dimensions of several aspects of the inner tube and the winged outer shield of the invention were provided to show a preferred embodiment, it will be recognized that other dimensions could be utilized. Similarly while particular materials and weight percentages were described, other materials and/or percentages could be utilized. Also, while certain terminology such as "circumferential" was used in describing the grooves on the inner tube and the protrusion and ramps of the winged shield, it will be appreciated that such terminology is intended to be broad in scope to encompass a groove in the circumference of the inner tube and protrusions and ramps in the on the inner surface of the of the outer shield regardless of the circumferential shape. Therefore, it will be apparent to those skilled in the art that yet other changes and modifications may be made to the invention as described without departing from the scope of the invention as so claimed.

I claim:

1. A medical device for assembly with a hollow needle, comprising:
   a) an inner tube member having
      a passageway therethrough,
      a front end through which the hollow needle can extend,
      a rear end with said passageway extending therethrough; and
      an outer surface having a circumferential first groove, a shoulder forwardly adjacent said first groove and a first inner tube ramp rearwardly adjacent said first groove, a first end of said first inner tube ramp being located at said first groove and constituting a first abutment surface, said first inner tube ramp decreasing in circumference as it extends towards said rear end, wherein said shoulder subscribes a larger cross-section area through said inner tube member than said first inner tube ramp, and said shoulder terminates at its front end in a second abutment surface; and
   b) a resiliently flexible hollow outer shield member having
      an inner surface, most of said inner surface subscribing a slightly larger cross-section than most of said outer surface of said inner tube member,
      a front end having a substantially unrestricted opening therein for permitting said inner tube member to be loaded therethrough during assembly of said medical device,
      at least one winged member attached to and flexible extending outwardly from said shield member,
      a rear end having an opening therein;
      first and second ramps located towards said rear end of said outer shield member, extending inwardly from said inner surface of said outer shield member, and subscribing smaller cross-sectional areas as they extend toward said rear end, said first ramp being forward of said second ramp and terminating in a third abutment surface, said second ramp terminating in a protrusion, said first range at said third abutment surface subscribing a substantially larger diameter than said second ramp at said protrusion, wherein the cross-sectional area subscribed by said protrusion of said outer shield member is substantially smaller than the circumference of said shoulder of said inner tube member, and wherein in a first locking position said outer shield member is in locking engagement with said inner tube member, said third abutment surface is forward of said second abutment surface, said shoulder engages said inner surface of said outer shield member between said first and second ramps, and said first abutment surface is rearward of said rear end of said shield member such that attempted movement of said outer shield member backward relative to said inner tube member is stopped by abutment of said second and third abutment surfaces and by the abutment of said first abutment surface and the rear end of said outer shield member, and attempted movement of said shield member forward relative to said inner tube member is stopped by the engagement of said shoulder and said second ramp.

2. A medical device according to claim 1, wherein:
said first ramp of said outer shield member and said shoulder of said inner tube member are sized such that said first ramp engages but slides over said shoulder when differential force is applied between said outer shield member and said inner tube member.

3. A medical device according to claim 2, wherein:
said protrusion of said outer shield member and said shoulder of said inner tube member are sized such that said protrusion cannot slide over said shoulder when differential force is applied between said outer shield member and said inner tube member by hand.

4. A medical device according to claim 3, wherein:
said outer surface of said inner tube member further includes a circumferential second groove rearward of said circumferential first groove.

5. A medical device according to claim 4, wherein:
said second groove is located substantially toward the rear end of said inner tube member, and said second groove terminates at its front end in a second inner tube ramp increasing in circumference as it extends towards the front end of said inner tube, and terminating at its rear end in a fourth abutment surface, such that in a retracted position, said protrusion disengageably engages said second groove.

6. A medical device according to claim 5, wherein:
said second inner tube ramp terminates at a front end at a third inner tube ramp which decreases in circumference as it extends towards the front end of said inner tube, said third inner tube ramp terminating in a valley which is of reduced circumference relative to and which lies between said first and third inner tube ramps.

7. A medical device according to claim 5, wherein:
in said retracted position, said second ramp of said outer shield member engages said second inner tube ramp, and said fourth abutment surface extends beyond the rear end opening of said outer shield member so a to prevent accidental disengagement of said protrusion from said second groove.

8. A medical device according to claim 5, further comprising:
c) said hollow needle extending throughout said passageway and terminating on one end forward of said front end of said inner tube member and on the other end in the vicinity of or beyond said rear end of said inner tube member, wherein said inner tube member is molded around said hollow needle.

9. A medical device according to claim 1, wherein:
said outer surface of said inner tube member further includes a circumferential second groove rearward of said circumferential first groove.

10. A medical device according to claim 9, wherein:
said second groove is located substantially toward the rear end of said inner tube member, and said second groove terminates at its front end in a second inner tube ramp increasing in circumference as it extends towards the front end of said inner tube, and terminating at its rear end in a fourth abutment surface, such that in a retracted position, said protrusion disengageably engages said second groove.

11. A medical device according to claim 10, wherein:
said second inner tube ramp terminates at its front end at a third inner tube ramp which decreases in circumference as it extends towards the front end of said inner tube member, said third inner tube ramp terminating in a valley which is of reduced circumference relative to and which lies between said first and third inner tube ramps.

12. A medical device according to claim 10, wherein:
in said retracted position, said second ramp of said outer shield member engages said second inner tube ramp, and said fourth abutment surface extends beyond the rear end opening of said outer shield member so as to prevent accidental disengagement of said protrusion from said second groove.

13. A medical device according to claim 1, wherein:
at least one of said inner tube member and said outer shield member is substantially non-cylindrical in shape, wherein the relative shapes of said inner tube member and outer shield member prevents rotation of said inner tube member relative to said outer shield member when said inner tube member and said outer shield member are engaged.

14. A medical device according to claim 13, wherein:
said outer shield member includes an outer surface with a substantially flat surface for placement adjacent the skin of a patient.

15. A medical device according to claim 14 wherein:
the cross-section through most of said inner surface of said outer shield member is a shape chosen from one of a truncated circle and a truncated oval.

16. A medical device according to claim 15, wherein:
the cross-section through said outer surface of said inner tube member is a shape chosen from one of a truncated circle and a truncated oval.

17. A medical device according to claim 13, wherein:
said outer shield member includes a plurality of finger grip ribs extending outwardly from said outer surface of said outer shield member.

18. A medical device according to claim 1, wherein:
said rear end of said inner tube member includes means for attaching at least one of a fluid conduit means and a fluid container means thereto.

19. A medical device according to claim 1, further comprising:
  c) said hollow needle extending throughout said passageway and terminating on one end forward of said front end of said inner tube member and on the other end in the vicinity of or beyond said rear end of said inner tube member, wherein said inner tube member is molded around said hollow needle.

20. A medical device for assembly with a hollow needle, comprising:
  a) an inner tube member having
    a passageway therethrough,
    a front end through which the hollow needle can extend,
    a rear end through which said passageway extends, and
    an outer surface with first locking means; and
  b) a resiliently flexible hollow outer winged shield member having
    a front end having a substantially unrestricted opening therein for permitting said inner tube member to be loaded therethrough during assembly of said medical device,
    at least one winged member attached to and flexibly extending outwardly from said shield member,
    a rear end having an opening therein, and
    an inner surface with second locking means,
  wherein said first locking means and second locking means comprise means for engaging said inner tube member and said outer shield member in a locked shielding position with said outer shield member surrounding and shielding the hollow needle such that said outer shield member cannot be substantially moved forward or backward relative to said inner tube member so as to reexpose the hollow needle through use of manual force on said inner tube member and said outer shield member.

21. A medical device according to claim 20, wherein:
said outer surface of said inner tube member said includes second engaging means for disengageably engaging said second locking means such that when said outer shield member is engaged with said inner tube member in a retracted position the hollow needle is exposed and such that an application of a differential axial force on said outer shield member relative to said inner tube member will cause said second engaging means and said second locking means to disengage.

22. A medical device according to claim 21 wherein:
said first locking means is comprised of a circumferential first groove, a shoulder forwardly adjacent said first groove, and a first inner tube ramp rearwardly adjacent said first groove, a first end of said first inner tube ramp being located at said first groove and constituting a first abutment surface, said first inner tube ramp decreasing in circumference as it extends towards said rear end of said inner tube member, wherein said shoulder subscribes a larger cross-section area through said inner tube member than said first inner tube ramp, and said shoulder terminates at its front end in a second abutment surface, said second locking means is comprised of a protrusion and first and second ramps located towards said rear end of said outer shield member, said first and second ramps extending inwardly from said inner surface of said outer shield member, and subscribing smaller cross-sectional areas as they extend toward said rear end, said first ramp being forward of said second ramp and terminating in a third abutment surface, said second ramp terminating in said protrusion, said first ramp at said third abutment surface subscribing a substantially larger diameter than said second ramp at said protrusion, and said second engaging means is comprised of a second inner tube ramp, a fourth abutment surface, and a circumferential second groove, said circumferential second groove rearward of said circumferential first groove and located substantially toward the rear end of said inner tube member and terminating at its front end in said second inner tube ramp, said second inner tube ramp increasing in circumference as it extends towards the front end of said inner tube, and terminating at its rear end in said fourth abutment surface.

23. A medical device according to claim 22, wherein:
said second inner tube ramp terminates at its front end at a third inner tube ramp which decreases in circumference as it extends towards the front end of said inner tube, said third inner tube ramp terminating in a valley which is of reduced circumference relative to and which lies between said first and third inner tube ramps, said outer shield member protrusion being slidable over said valley from said retracted position in which said engaging means engages said first locking means to said shielding position in which said outer shield member is in locking engagement with said inner tube member such that said shoulder engages said inner surface of said outer shield member between said first and second ramps, and said first abutment surface is rearward of said rear end of said shield member such that attempted movement of said outer shield member backward relative to said inner tube member is stopped by abutment of said second and third abutment surfaces, and by the abutment of said first abutment surface and the rear end of said outer shield member, and attempted movement of said shield member forward relative to said inner tube member is stopped by the engagement of said shoulder and said second ramp.

24. A medical device according to claim 20, further comprising:
  c) said hollow needle extending throughout said passageway and terminating on one end forward of said front end of said inner tube member and on the other end in the vicinity of or beyond said rear end of said inner tube member, wherein said inner tube member is molded around and to said hollow needle.

25. A medical device for assembly with a hollow needle, comprising:
  a) an inner tube member having
    a passageway therethrough,
    a front end through which the hollow needle can extend,
    a rear end through which said passageway extends, and a rear end through which said passageway extends, and an outer surface having a circumferential first groove, a shoulder forwardly adjacent said first groove and a first inner tube ramp rearwardly adjacent said first groove, a first end of said first inner tube ramp being located at said first groove and constituting a first abutment surface, said first inner tube ramp decreasing in circumference as it extends towards said rear end, wherein said shoulder subscribes a larger cross-section area through said inner tube member than said first inner tube ramp, and said shoulder terminates at its front end in a second abutment surface; and b) a resiliently flexible hollow outer shield member having an inner surface, most of said inner surface subscribing a slightly larger cross-section than most of said outer surface of said inner tube member, a front end having a substantially unrestricted opening therein for permitting said inner tube member to be loaded therethrough during assembly of said medical device, at least one winged member attached to and flexibly extending outwardly from said shield member, a rear end having an opening therein, a first protrusion and a first shield member ramp located towards said rear end of said outer shield member and extending inwardly from said inner surface of said outer shield member, said first shield member ramp subscribing smaller cross-sectional areas as it extends toward said rear end, said first protrusion being forward of said first shield member ramp and terminating in a third abutment surface, said first shield member ramp terminating in a second protrusion, said first protrusion at said third abutment surface subscribing a substantially larger diameter than said second ramp at said second protrusion, wherein the cross-sectional area subscribed by said second protrusion of said outer shield member is substantially smaller than the circumference of said shoulder of said inner tube member, and wherein in a first locking position, said outer shield member is in locking engagement with said inner tube member, said third abutment surface is forward of said second abutment surface, said shoulder engages said inner surface of said outer shield member between said first protrusion and said first shield member ramp, and said first abutment surface is rearward of said rear end of said shield member such that attempted movement of said outer shield member backward relative to said inner tube member is stopped by abutment of said second and third abutment surfaces, and by the abutment of said first abutment surface and the rear end of said outer shield member, and attempted movement of said shield member forward relative to said inner tube member is stopped by the engagement of said shoulder and said second ramp.

26. A medical device according to claim 25, wherein said first protrusion of said outer shield member and said shoulder of said inner tube member are sized and shaped such that said first protrusion engages but slides over said shoulder when differential force is applied between said outer shield member and said inner tube member, and said second protrusion of said outer shield member and said shoulder of said inner tube member are sized such that said second protrusion cannot slide over said shoulder when differential force is applied between said outer shield member and said inner tube member by hand.

27. A medical device according to claim 26, wherein: said outer surface of said inner tube member further includes a circumferential second groove rearward of said circumferential first groove and located substantially toward the rear end of said inner tube member, and said second groove terminates at its front end in a second inner tube ramp increasing in circumference as it extends towards the front end of said inner tube, and terminating at its rear end in a fourth abutment surface, such that in a retracted position, said second protrusion disengageably engages said second groove.

28. A medical device according to claim 27, wherein: said second inner tube ramp terminates at a front end at a third inner tube ramp which decreases in circumference as it extends towards the front end of said inner tube, said third inner tube ramp terminating in a valley which is of reduced circumference relative to and which lies between said first and third inner tube ramps, and in said retracted position, said first shield member ramp engages said second inner tube ramp, and said fourth abutment surface extends beyond the rear end opening of said outer shield member so as to prevent accidental disengagement of said second protrusion from said second groove.

29. A medical device according to claim 28, further comprising:

c) said hollow needle extending throughout said passageway and terminating on one end forward of said front end of said inner tube member and on the other end in the vicinity of or rearward of said rear end of said inner tube member, wherein said inner tube member is molded around said hollow needle.

30. A medical device according to claim 25, wherein: said rear end of said inner tube member includes means for attaching at least one of a fluid conduit means and a fluid container means thereto.

* * * * *